US010258570B2

(12) United States Patent
Gessler et al.

(10) Patent No.: US 10,258,570 B2
(45) Date of Patent: Apr. 16, 2019

(54) LIPOSOMES FOR PULMONARY ADMINISTRATION

(75) Inventors: Tobias Gessler, Wettenberg (DE); Thomas Schmehl, Gießen (DE); Monika Rieger, Spiesen-Elversberg (DE)

(73) Assignee: Lung Biotechnology Inc., Silver Spring, MD (US)

( * ) Notice: Subject to any disclaimer, the term of this patent is extended or adjusted under 35 U.S.C. 154(b) by 686 days.

(21) Appl. No.: 13/386,006

(22) PCT Filed: Jun. 29, 2010

(86) PCT No.: PCT/EP2010/059216
§ 371 (c)(1),
(2), (4) Date: Oct. 11, 2012

(87) PCT Pub. No.: WO2011/000835
PCT Pub. Date: Jan. 6, 2011

(65) Prior Publication Data

US 2013/0039847 A1 Feb. 14, 2013

(30) Foreign Application Priority Data

Jun. 30, 2009 (DE) ........................ 10 2009 031 274

(51) Int. Cl.
*A61K 9/127* (2006.01)
*A61K 9/00* (2006.01)

(52) U.S. Cl.
CPC ............ *A61K 9/127* (2013.01); *A61K 9/0078* (2013.01)

(58) Field of Classification Search
CPC ...................................................... A61K 9/127
(Continued)

(56) References Cited

U.S. PATENT DOCUMENTS 4,732,914 A 3/1988 Morton, Jr.
4,895,452 A * 1/1990 Yiournas ............... B01F 5/0057 264/4.1
(Continued)

FOREIGN PATENT DOCUMENTS

EP 0 126 580 B1 11/1984
EP 0 361 894 B1 4/1990
(Continued)

OTHER PUBLICATIONS

J.E. Trosko, Mutation Research 480-481, pp. 219-229, 2001.*
(Continued)

*Primary Examiner* — Gollamudi Kishore
(74) *Attorney, Agent, or Firm* — Foley & Lardner LLP

(57) ABSTRACT

The invention relates to liposomes for pulmonary application, advantageously comprising at least one first and at least one second phospholipid, cholesterol, and at least one active substance and/or colorant, wherein the first phospholipid is a phosphatidylcholine, preferably DSPC, and the second phospholipid is a phosphatidylcholine or an ethanolamine, preferably selected from the group DMPC, DPPC, DPPE. It is thereby advantageous if the first and the second phospholipid are present at a molar ratio of 0.5:1 to 10:1, preferably at a ratio of 6:1 to 2:1, in particular preferably at a ratio of 3:1. It is further advantageous if the molar ratio between phospholipids and cholesterol is between 10:1 and 1:1, preferably between 6:1 and 3:1, in particular preferably 4:1. The second phospholipid is further preferably DMPC or DPPE, in particular preferably DPPE. The size of the liposomes is advantageously between 0.05 μm and 5 μm, preferably between 0.2 μm and 2.0 μm, and the median aerodynamic mass diameter of aerosol particles comprising the liposomes is between 1 μm and 6 μm, preferably between 1.5 μm and 5 μm, in particular preferably between 2 μm and 4.5 μm. It is further in particular advantageous if the
(Continued)

Figure 3:
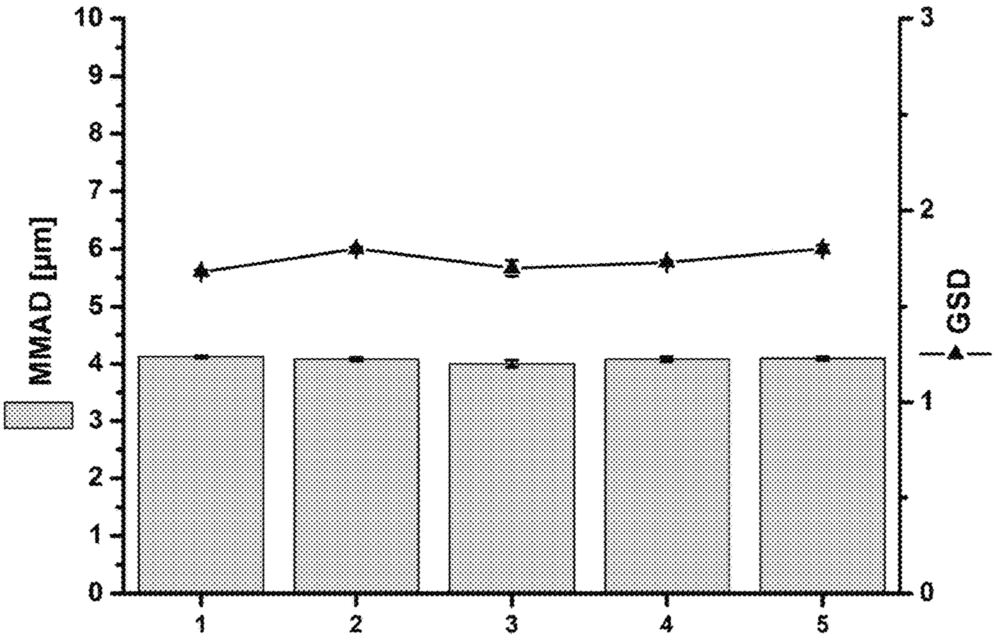

liposomes comprise an atomization stability of greater than 50%, preferably greater than 75%, in particular preferably greater than 80%, and if the transition temperature is greater than 37° C., preferably greater than 45° C., in particular preferably greater than 50° C.

24 Claims, 5 Drawing Sheets

(58) Field of Classification Search
USPC .......................................................... 424/450
See application file for complete search history.

(56) References Cited

U.S. PATENT DOCUMENTS

| | | | | |
|---|---|---|---|---|
| 4,895,719 | A | 1/1990 | Radhakrishnan et al. | |
| 4,999,208 | A * | 3/1991 | Lengerich | A21D 8/02 426/243 |
| 5,006,343 | A | 4/1991 | Benson et al. | |
| 5,049,388 | A | 9/1991 | Knight et al. | |
| 5,230,899 | A * | 7/1993 | Park | A61K 9/1277 264/4.1 |
| 5,306,483 | A | 4/1994 | Nautone | |
| 5,340,587 | A | 8/1994 | Mihalko et al. | |
| 5,580,575 | A | 12/1996 | Unger et al. | |
| 5,585,112 | A | 12/1996 | Unger et al. | |
| 5,662,929 | A | 9/1997 | Lagace et al. | |
| 5,715,824 | A | 2/1998 | Unger et al. | |
| 5,783,566 | A | 7/1998 | Mislick | |
| 5,814,335 | A | 9/1998 | Webb et al. | |
| 6,103,259 | A * | 8/2000 | Roux | A61K 8/14 264/4.1 |
| 6,113,946 | A | 9/2000 | Szoka, Jr. et al. | |
| 6,193,997 | B1 | 2/2001 | Modi | |
| 6,443,898 | B1 | 9/2002 | Unger et al. | |
| 6,764,693 | B1 | 7/2004 | Smith | |
| 6,793,912 | B2 | 9/2004 | Pilkiewicz et al. | |
| 7,138,136 | B2 | 11/2006 | Annapragada et al. | |
| 7,384,978 | B2 | 6/2008 | Phares et al. | |
| 7,417,070 | B2 | 8/2008 | Phares et al. | |
| 7,544,713 | B2 | 6/2009 | Phares et al. | |
| 8,591,942 | B2 * | 11/2013 | Javeri | A61K 9/1278 264/4.1 |
| 2001/0055610 | A1 | 12/2001 | Nagata et al. | |
| 2002/0034537 | A1 * | 3/2002 | Schulze | A61K 9/127 424/450 |
| 2003/0059375 | A1 | 3/2003 | Perez-Soler et al. | |
| 2003/0124180 | A1 | 7/2003 | Ebert et al. | |
| 2003/0152618 | A1 * | 8/2003 | Fisher | A61K 49/1812 424/450 |
| 2003/0232019 | A1 | 12/2003 | Basu et al. | |
| 2004/0009231 | A1 | 1/2004 | Jackson et al. | |
| 2005/0008617 | A1 | 1/2005 | Chen et al. | |
| 2005/0207986 | A1 * | 9/2005 | Schutt | A61K 9/0075 424/45 |
| 2005/0282901 | A1 * | 12/2005 | Phares | C07C 59/70 514/571 |
| 2006/0002992 | A1 | 1/2006 | Schmehl et al. | |
| 2006/0141029 | A1 | 6/2006 | Heller et al. | |
| 2006/0141047 | A1 | 6/2006 | Heller et al. | |
| 2007/0031342 | A1 * | 2/2007 | Tzannis | A61K 38/23 424/45 |
| 2007/0077290 | A1 | 4/2007 | Li et al. | |
| 2007/0110798 | A1 * | 5/2007 | Drummond | A61K 9/0019 424/450 |
| 2008/0317839 | A1 * | 12/2008 | Quay | C07D 233/64 424/450 |
| 2009/0074848 | A1 | 3/2009 | Johnstone et al. | |
| 2009/0269396 | A1 * | 10/2009 | Cipolla | A61K 9/0073 424/450 |
| 2009/0324698 | A1 * | 12/2009 | Wagner | A61K 9/0034 424/450 |
| 2010/0119587 | A1 * | 5/2010 | Amighi | A61K 9/1617 424/450 |
| 2012/0177693 | A1 * | 7/2012 | Cipolla | A61K 31/191 424/400 |

FOREIGN PATENT DOCUMENTS

| | | | |
|---|---|---|---|
| WO | WO-86/06959 | A1 | 12/1986 |
| WO | WO 87/05803 | A1 | 10/1987 |
| WO | WO-02/03959 | A1 | 1/2002 |
| WO | 03/084507 | * | 10/2003 |
| WO | WO-03/084507 | A2 | 10/2003 |
| WO | WO-2004/112695 | A2 | 12/2004 |
| WO | WO-2006/12446 | A2 | 11/2006 |
| WO | WO 2009/070609 | A2 | 6/2009 |
| WO | WO 2009/127060 | A1 | 10/2009 |
| WO | WO-2009/129395 | A1 | 10/2009 |

OTHER PUBLICATIONS

International Search Report in PCT/EP2010/059216 (dated Dec. 21, 2010).
Written Opinion in PCT/EP2010/059216 dated Dec. 21, 2010.
International Preliminary Report on Patentability in PCT/EP2010/059216 dated Jan. 17, 2012.
Kleemann E. et al., "Iloprost-Containing Liposomes for Aerosol Application in Pulmonary Arterial Hypertension: Formulation Aspects and Stability," *Pharmaceutical Research*, 24(2):277-87 (Feb. 2007) (published online Dec. 27, 2006).
Hunt et al., "Engodenous Airway Acidification," Am. J. Respir. Crit. Care Med., 2000, 161:694-699.
Max et al. "Inhaled prostacyclin in the treatment of pulmonary hypertension," Eur. J. Pediatr., 1999, 158(Supp.1):S23-S26.
Singh et al., "Stealth monensin liposomes as a potentiator of adriamycin in cancer treatment," Journal of Controlled Release, 1999, 59:43-53.
Taylor et al., "Liposomes for controlled delivery of drugs to the lung," Thorax, 1992, 47:257-259.

* cited by examiner

Fig. 1

| Embodiment variant | P1 | P2 | Molar ratio P1:P2: Chol | Molar ratio P1:P2 | Molar ratio PL:Chol |
|---|---|---|---|---|---|
| 1 | DSPC | DPPC | 4:4:2 | 1:1 | 4:1 |
| 2 | DSPC | DMPC | 6:1:2 | 6:1 | 3.5:1 |
| 3 | DSPC | DPPE | 6:2:2 | 3:1 | 4:1 |

Fig. 2

| | Embodiment var. 1 DSPC/DPPC/Chol | Embodiment var. 2 DSPC/DMPC/Chol | Embodiment var. 3 DSPC/DPPE/Chol |
|---|---|---|---|
| EE [%] | 1.29±0.18 | 1.99±0.21 | 2.78±0.30 |
| $CF_{lip}$PRE [%] | 96.1±2.1 | 96.6±0.8 | 99.6±0.2 |
| $CF_{lip}$POST [%] | 79.1±2.6 | 80.3±0.9 | 83.8±2.8 |
| Stability during nebulization | 82 % | 83 % | 84 % |
| Size of liposomes before neb. [µm] | 0.59±0.04 | 0.61±0.02 | 0.62±0.02 |
| Size of liposomes after neb. [µm] | 0.59±0.02 | 0.64±0.09 | 0.73±0.13 |

| | | |
|---|---|---|
| 1: | Control: | Aerosolized solution of 0.9 % NaCl |
| 2: | State of the art: | Liposomes comprising DPPC/DMPC/Chol |
| 3: | Embodiment var. 1: | Liposomes comprising DSPC/DPPC/Chol |
| 4: | Embodiment var. 2: | Liposomes comprising DSPC/DMPC/Chol |
| 5: | Embodiment var. 3: | Liposomes comprising DSPC/DPPE/Chol |

| | | | |
|---|---|---|---|
| 6: | ■ | State of the art: | Liposomes comprising DPPC/DMPC/Chol |
| 7: | ● | Embodiment variant 1: | Liposomes comprising DSPC/DPPC/Chol |
| 8: | ◆ | Embodiment variant 2: | Liposomes comprising DSPC/DMPC/Chol |
| 9: | ▲ | Embodiment variant 3: | Liposomes comprising DSPC/DPPE/Chol |
| 10: | ○ | Control: | Free carboxyfluorescein |

6: ■ State of the art: Liposomes comprising DPPC/DMPC/Chol

7: ● Embodiment variant 1: Liposomes comprising DSPC/DPPC/Chol

8: ◆ Embodiment variant 2: Liposomes comprising DSPC/DMPC/Chol

9: ▲ Embodiment variant 3: Liposomes comprising DSPC/DPPE/Chol

10: ○ Control: Free carboxyfluorescein

| | | | |
|---|---|---|---|
| 6 ■ | State of the art: | Liposomes comprising DPPC/DMPC/Chol |
| 7 ● | Embodiment variant 1: | Liposomes comprising DSPC/DPPC/Chol |
| 8 ◆ | Embodiment variant 2: | Liposomes comprising DSPC/DMPC/Chol |
| 9 ▲ | Embodiment variant 3: | Liposomes comprising DSPC/DPPE/Chol |
| 10 ○ | Control: | Free carboxyfluorescein |

LIPOSOMES FOR PULMONARY ADMINISTRATION

BACKGROUND OF THE INVENTION

Field of the Disclosure

The invention concerns liposomes for pulmonary administration as well as aerosol particles and pharmaceutical compositions containing the same.

Description of the Related Technology

The generally known pharmaceutical term "liposomes" denotes colloidal particles which form spontaneously when phospholipids are dispersed in an aqueous medium. A particular advantageous feature for a medical application of such liposomes is that during the formation of liposomes, phospholipids organize in form of a membrane which is very similar to the natural membrane of cells and cell organelles. Simultaneously, a certain fraction of the aqueous solution is encapsulated in the inner compartment of liposomes, which therefore can be used for the delivery of lipophilic—i.e. membrane-bound—and hydrophilic—i.e. solubilized in the encapsulated aqueous compartment—therapeutic agents.

A number of options are known for the administration of supported and unsupported drug compounds. Common practice is to administer pharmaceutical formulations orally, for example in form of tablets or as liquids. Disadvantageous in this case is however that carrier and/or active compounds—unless directly determined for gastric release—first have to withstand the aggressive gastric environment prior to absorption in the intestines and release into the bloodstream. In addition, these substances subsequently have to be transported through the body to their final place of destination. A precise and target-oriented drug delivery into the diseased organ or specific tissue, respectively, is therefore only possible to a limited degree. Instead, also healthy organs and tissues are supplied with drugs which may in that case even exhibit harmful effects, thus often leading to undesirable adverse reactions. At the same time, the amount of active compound which de facto reaches the target site is drastically reduced due to this effect. It is consequently often necessary to administer a considerably higher amount of in many cases expensive drug compound than effectively required for therapy.

In order to circumvent this problem, efforts are made to find a route of administration to the target site or the immediate vicinity thereof which bypasses the gastrointestinal tract. In addition to for example an intravenous, intraperitoneal or intramuscular administration, particularly the inhalation of drug compounds turned out to be advantageous and acceptable for the patient. An inhalative administration is for example suitable for the treatment of systemic diseases like e.g. diabetes mellitus and advantageous for the treatment of respiratory tract diseases, for example pulmonary hypertension (cf. Kleemann et al., Pharmaceutical Research, Vol 24, No. 2, February 2007), but also COPD, asthma and pneumonia. A considerable disadvantage of conventional aerosol therapies is the often short duration of action of inhaled drug compounds. As a result, inhalations in most cases have to be carried out in short intervals. The treatment of pulmonary hypertension with inhaled Iloprost for example requires up to 12 daily inhalations with a duration of approximately 10 minutes each, which considerably reduces the patient's quality of life. Furthermore, relatively high local drug concentrations occur immediately during or after an inhalative administration, while basically no active compound is provided during inhalation breaks. This amongst others entails the risk that at night, when no inhalations are carried out, patients may quickly face a supply shortage of active compound.

A prerequisite for an efficient inhalative therapy is the delivery of aerosol particles into the lung, which in particular depends on the diameter and density of the particles utilized.

A further critical issue for an inhalative administration of liposomes is their stability during the nebulization process. During nebulization of suspensions and liquids, liposomes in the aerosol are often subjected to forces which may compromise liposome integrity, thus leading to a premature release of liposome-encapsulated compounds.

DE 102 14 983 A therefore provides liposomal formulations which can be nebulized for a pulmonary administration of active compounds. Main component of disclosed liposomal formulations is dipalmitoylphosphatidylcholine (DPPC), which is mixed at a ratio of 7:3 or 7:4, with cholesterol (Chol). In addition, as third component dimyristoylphosphatidylcholine (DMPC), polyethylene glycol (PEG) or sphingomyelin (SM) is added. Said liposomes are nebulized and can be inhaled in this form by the patient. Disadvantageous of these formulations is however in particular the limited stability of liposomes during the nebulization process. As a matter of fact, only a fraction of intact drug-loaded liposomes reaches the lung after nebulization. Furthermore, these liposomes display only a limited controlled release effect in the lung.

Desirable instead would be a retarded release of the active compound from a liposomal formulation after pulmonary administration over a prolonged period of time, which is aimed at a continuous supply of the drug compound.

Aim of the present invention is therefore to overcome these and other disadvantages of the state-of-the-art and to provide liposomes which exhibit a high stability during nebulization. At the same time, aerosols prepared from liposomal formulations should be able to easily reach the lung and provide biologically compatible liposomes which also allow for a sustained release of enclosed active substances and/or dyes in the target tissue. Furthermore, the preparation of said liposomes should be convenient, reliable and cost-effective. Beyond this, the possibility shall be provided to prepare pharmaceutical formulations which are suitable for the prevention, diagnosis and/or treatment of systemic diseases and lung diseases.

Features of the invention address one or more of the shortcomings noted above.

SUMMARY OF THE INVENTION

To solve the problem, the present invention provides liposomes for pulmonary administration, comprising at least a first and at least a second phospholipid as well as cholesterol and at least one drug compound and/or dye, whereby the first phospholipid is the phosphatidylcholine disteaorylphosphatidylcholine DSPC, and the second phospholipid is a phosphatidylcholine or an ethanolamine, preferably chosen from the group of dimyristoylphosphatidylcholine DMPC, dipalmitoylphosphatidylcholine DPPC, dipalmitoylphosphatidylethanolamine DPPE.

Said liposomes according to the present invention are able to deliver with high efficiency active compounds to a target site like for example the lung without a significant loss of liposome integrity during transportation. Furthermore, encapsulated active compounds are not suddenly released at the target site at once, but over a prolonged period of time. Liposomes according to the present invention are therefore particularly well suited for a use in applications where the active compound contained therein is destined for retarded delivery, for example a release corresponding to the sustained-release type. The patient is consequently spared multiple and time-consuming inhalations, and instead takes up with a single inhalation the entire amount of active substance which is required for a longer period of time. The active ingredient is however initially retained in the liposomes and continuously released into the target tissue in doses which are able to provide the desired therapeutic effect, while adverse effects caused by a drug overdose are avoided. A continuous supply with active compound on a constant level is thus guaranteed. The patient's quality of life is positively influenced, due to a lower number of inhalations required.

All this is especially favorable if the second phospholipid is DMPC or DPPE, particularly preferred DPPE, and if the first and the second phospholipid are present in a molar ratio of 0.5:1 to 10:1, preferably in a ratio of 6:1 to 2:1, particularly preferred in a ratio of 3:1. In addition preferable is a molar ratio of phospholipids to cholesterol ranging between 10:1 and 1:1, preferably between 6:1 and 3:1, and particularly preferred is a molar ratio of 4:1.

It is furthermore of particular advantage if the stability of liposomes during nebulization is higher than 50%, preferably more than 75%, particularly preferred more than 80%. Such a high stability of liposomes prevents amongst others efficiently that during nebulization, non-encapsulated active compound is released into the inhalant due to a disintegration of liposomes. This consequently prevents an overdose or the occurrence of undesirable side effects caused by non-encapsulated active substance in the inhalant.

It is furthermore of advantage if the median diameter of liposomes ranges between 0.05 μm and 5 μm, preferably between 0.2 μm and 2.0 μm. Liposomes are thus smaller than aerosol particles formed during nebulization. These aerosol particles are small droplets which each contain a large number of liposomes according to the present invention. It is furthermore of advantage if the median aerodynamic volume diameter of aerosol particles which contain liposomes is between 1 μm and 6 μm, preferably between 1.5 μm and 5 μm, particularly preferred between 2 μm and 4.5 μm. With a view to the stability during nebulization, it becomes clear that the size of liposomes after nebulization advantageously differs by less than 1 μm, preferably by less than 0.2 μm from the size of the liposomes prior to nebulization.

Especially with respect to a retarded release of active compounds it is furthermore particularly favorable if the phase transition temperature of liposomes is higher than 37° C., preferred higher than 45° C., particularly preferred higher than 50° C. At a temperature below this phase transition temperature, liposomal phospholipids are arranged in a quasicrystalline lattice which is comparably rigid and inflexible. Enclosed active compounds are almost unable to cross the lipid membrane of these liposomes and are thus released only slowly and to a minor extent. Above the phase transition temperature, phospholipids are in a liquid crystalline state, allowing for a faster diffusion of enclosed substances through the liposome membrane. Active compounds are released very quickly in this case. It is quite obvious that, in case a sustained release of active compound is desired, a phase transition temperature of liposomes according to the present invention favorably should be higher than the body temperature, i.e. above 37° C.

It furthermore becomes obvious that liposomes according to the present invention are preferably nebulized with piezoelectric, air-jet or ultrasonic nebulizers or with soft-mist inhalators. In addition, said liposomes can be used for the preparation of pharmaceutical formulations which are suitable for the prevention, diagnosis and/or treatment of lung diseases and the treatment of systemic diseases.

As active compound, it is advantageous to use agents chosen from the group of appetite suppressants/antiadipose agents, acidose therapeutics, analeptics/antihypoxaemic agents, analgesics, antirheumatics, anthelmintics, antiallergics, antianemics, antiarrhythmics, antibiotics, antiinfectives, antidementives, antidiabetics, antidotes, antiemetics, antivertigo agents, antiepileptics, antihemorrhagic agents, haemostatics, antihypertensives, antihypoglycemics, antihypotensives, anticoagulants, antimycotics, antiparasitic agents, antiphogisitics, antitussives, expectorants, antiarteriosclerotics, beta-receptor blockers, calcium channel blockers, inhibitors of the renin-angiotensin-aldosterone system, broncholytics, anti-asthma agents, cholagogics, bile duct therapeutics, cholinergics, corticoids, diagnostics and agents for diagnostic preliminaries, diuretics, circulation-promoting agents, anti-addiction agents, enzyme inhibitors, enzyme-activating or stimulating agents, enzyme deficiency correcting compounds, receptor antagonists, transport proteins, fibrinolytics, geriatric agents, gout agents, influenza drugs, colds and flu remedies, gynecologic agents, hepatics, hypnotics, sedatives, hypophysis and hypothalamus hormones, regulatory peptides, hormones, peptide inhibitors, immunomodulators, cardiacs, coronary agents, laxants, lipid-reducing agents, local anaesthetics, neural therapeutic agents, gastric agents, migraine agents, mineral preparations, muscle relaxants, narcotics, neurotropic agents, osteoporosis remedies, calcium/calcium metabolism regulators, remedies for Parkinson's disease, psychopharmaceuticals, sinusitis agents, roborantia, thyroid therapeutics, serums, immunoglobulins, vaccines, antibodies, sexual hormones and their inhibitors, spasmolytics, anticholinergic agents, thrombocyte aggregation inhibitors, antituberculosis agents, urological agents, vein therapeutics, vitamins, cytostatics, antineoplastic agents, homeopathic remedies, vasoactive agents, gene therapeutics (DNA/RNA derivatives), transcription inhibitors, virostatics, nicotin, agents against erectile dysfunction, nitric oxide and/or nitric oxide-liberating substances.

In the sense of the present invention, also magnetic particles are included as potential active compounds and/or dyes. Said particles can for example be utilized in diagnostic imaging techniques, but also for therapeutic purposes, e.g. in chemo- and radiotherapy and in hyperthermia therapy.

The term "diagnostics" includes in vitro as well as also in vivo diagnostics. A diagnostic agent to be utilized according to the present invention can for example be image-producing and/or radioactive and/or a contrast agent.

Notably, the utilization of liposomes is of particular advantage for the preparation of a pharmaceutical composition for the prevention, diagnosis and/or treatment of diseases of the alveolar space as well as for the treatment of respiratory diseases and the utilization of liposomes for the preparation of a pharmaceutical composition for the prevention, diagnosis and/or treatment of pulmonary hypertension.

Liposomes according to the present invention can thus be utilized for the preparation of pharmaceutical compositions for the treatment of the following diseases: Inflammatory (infectious, non-infectious) and hyperproliferative (neoplastic, non-neoplastic) diseases of the lung and the respiratory tract such as bronchitis, COPD, asthma, pneumonia, tuberculosis, pulmonary hypertension, lung tumors, fibrotic lung diseases, furthermore lung metastases, cystic fibrosis, sarcoidosis, aspergillosis, bronchiectasis, ALI, IRDS, ARDS, alveolar proteinosis, immunosuppression and prophylaxis against infection after lung transplantation.

Conceivable is also a utilization in the case of sepsis, disorders of fat metabolism, tumor diseases, leukemias, innate metabolic disorders (e.g. growth disorders, storage disorders, disorders of the iron metabolism), endocrine diseases for example of the pituitary or the thyroid (Glandula thyreoidea), diabetes, obesity, psychological disorders (e.g. schizophrenia, depression, bipolar affective disorders, posttraumatic stress syndrome, anxiety and panic disorders), CNS disorders (for example M. Parkinson, multiple sclerosis, epilepsy), infectious diseases, rheumatic diseases, allergic and autoimmune diseases, erectile dysfunctions, cardiovascular diseases (for example arterial hypertension, coronary heart diseases, cardiac arrhythmias, heart failure, thromboses and embolisms), renal failure, anaemias, antibody deficiencies, innate or acquired coagulation disorders, platelet function disorders or vitamin deficiency syndromes.

BRIEF DESCRIPTION OF THE DRAWING FIGURES

Figure 4A:
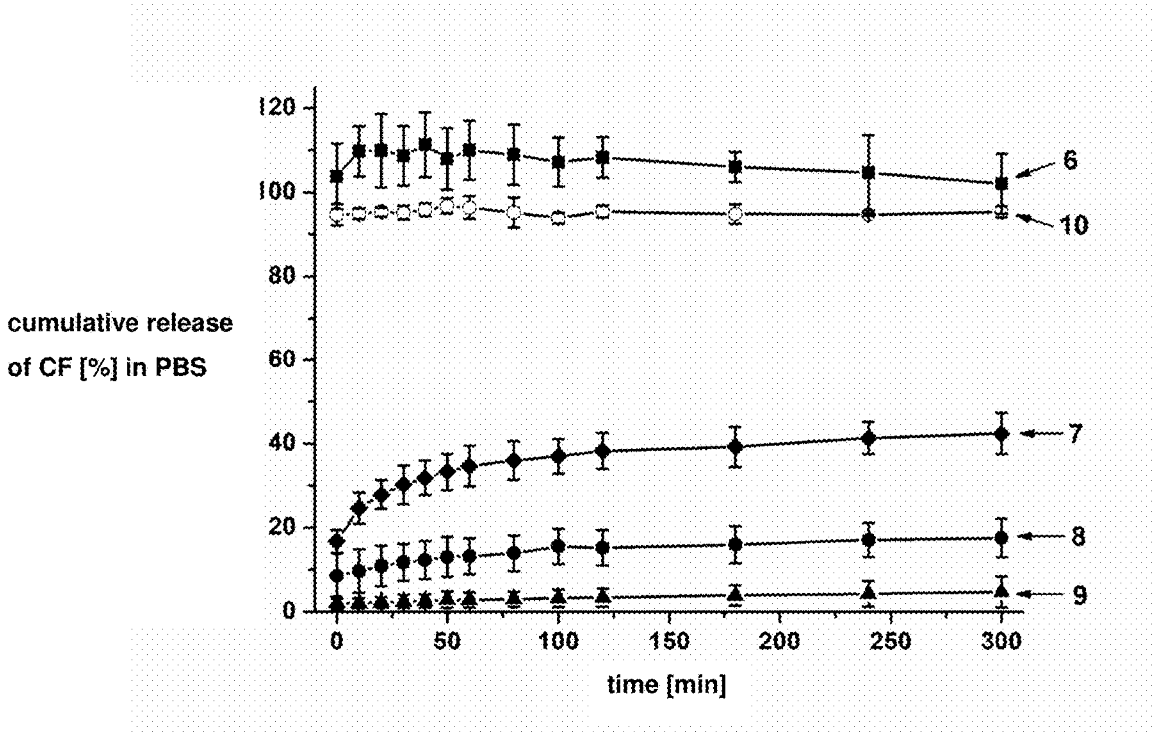
Figure 4B:
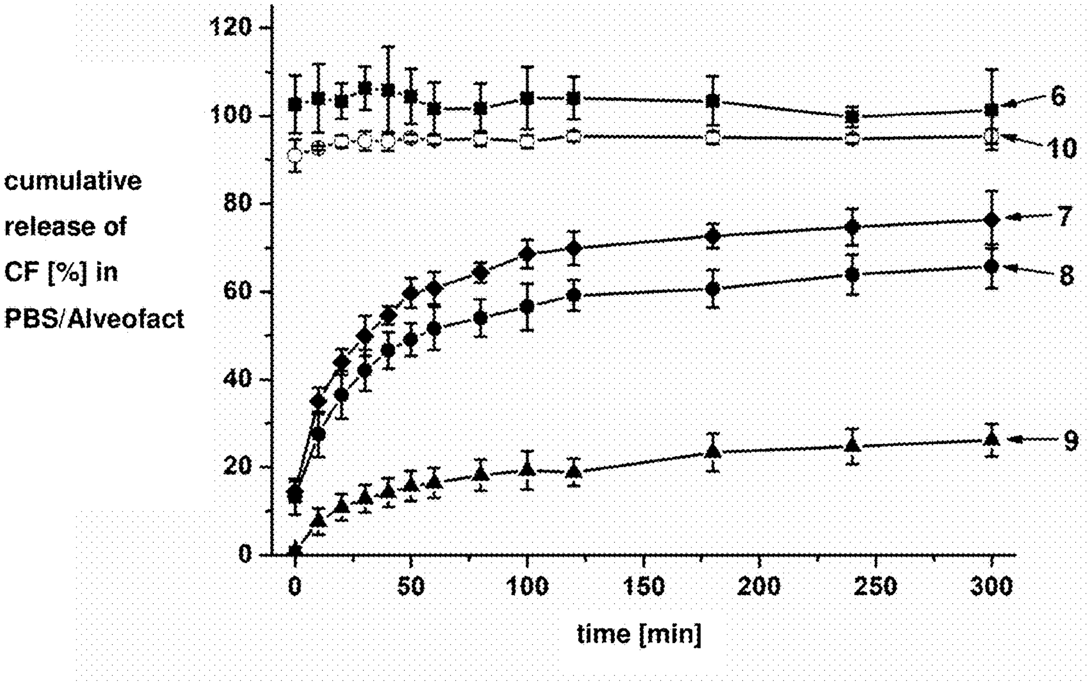
Figure 5:
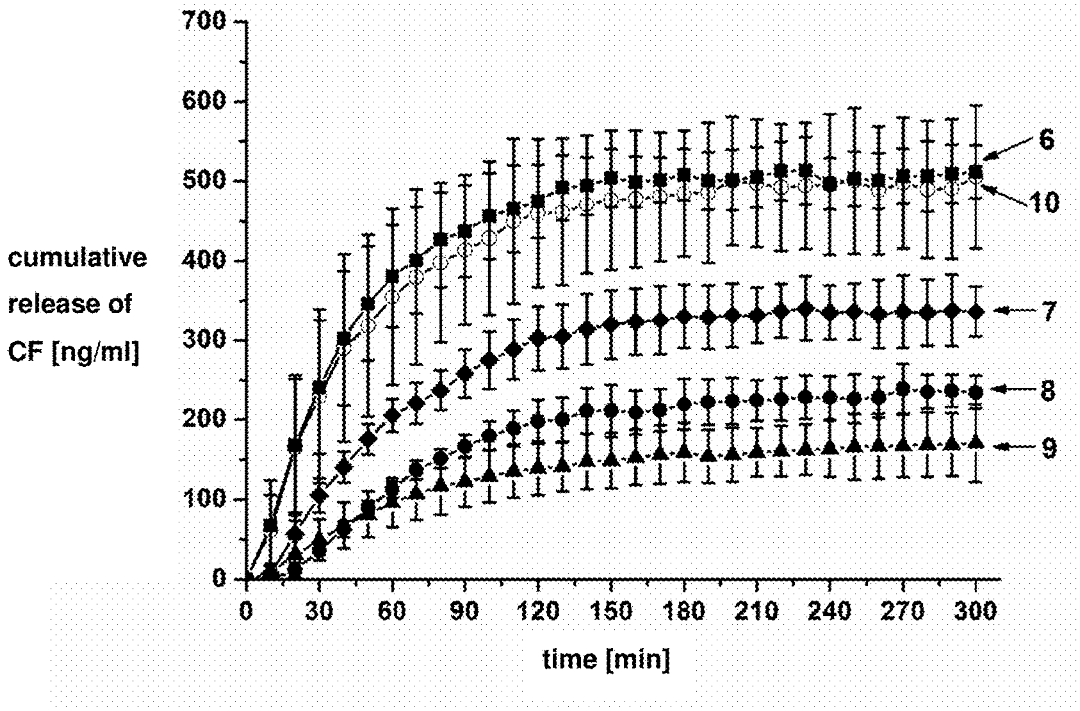

Further features, details and advantages of the present invention can be gathered from the wording of the claims as well as from the following description of exemplary embodiments and presented figures, which show:

FIG. 1 liposomal formulations of exemplary embodiments 1, 2 and 3,

FIG. 2 encapsulation efficiency and stability of liposomes after nebulization, FIG. 3 parameters of aerosol particle size distribution (MMAD, GSD) of different liposome dispersions, FIG. 4*a* release characteristics of different drug-loaded liposomes in PBS, FIG. 4*b* release characteristics of different drug-loaded liposomes in PBS/surfactant, FIG. 5 release characteristics of different drug-loaded liposomes in the isolated organ model.

DETAILED DESCRIPTION

In order to characterize the features of liposomes according to the present invention in more detail, three exemplary embodiments for liposomal formulations are specified with respect to encapsulation efficiency, drug load after nebulization (stability), phase transition temperature, aerosol particle and liposome size, as well as drug release characteristics.

In all three examples, the water-soluble fluorescent dye carboxyfluorescein CF is used as model drug substance. Depending on the desired application of liposomes, any other water-, fat soluble or amphiphilic substance is however conceivable, for example iloprost, sildenafil, treprostinil, antihypertensive agents, insulin, various antibiotics etc., or also a vital dye, contrast medium or any other marker. Said liposomes can thus also be used for e.g. diagnostic purposes.

Liposomal formulations are each prepared according to the commonly known film method as follows:

A mixture according to the present invention of first and second phospholipid P1, P2, PL with cholesterol Chol (150 mg total, for molar ratios of the lipid composition refer to FIG. 1 and embodiments 1 to 3) is dissolved in 40 ml of a solvent mixture consisting of seven parts of chloroform and three parts of methanol.

Subsequently, the solvent is removed by incubation in a rotary evaporator (for example Rotavapor M. Büchi Labortechnik, Flawil, CH) for one hour under low pressure and at a temperature above the phase transition temperature of the lipid mixture. As a result, a thin lipid film is obtained which is allowed to dry under vacuum for an additional hour.

The model drug substance carboxyfluorescein CF is dissolved in PBS buffer with a pH value of 7.4 in a concentration of 50 mg/ml. This solution is heated to 65° C.

After the drying of the lipid film, 10 ml of the heated carboxyfluorescein-containing buffer solution are added to the lipid film. To induce an encapsulation of the model drug substance, the flask containing the rehydrated lipid film is rotated for two hours at 65° C. In order to stabilize the bilayer membranes in the resulting dispersion of multilamellar liposomes, the dispersion is subsequently kept for one hour at 4° C.

Then the size of vesicles generated by these means in the dispersion is reduced. For this purpose, the dispersion is extruded 21 times at 70° C. using a hand-extruder (for example Liposofast, Avestin, Ottawa, Canada) through a 400 nm polycarbonate membrane (for example by Avestin, Mannheim, Germany). The resulting liposomes are again stored for 20 hours at 4° C. for stabilization.

To separate carboxyfluorescein-loaded liposomes from the non-encapsulated, free carboxyfluorescein CF still present in the solution, the dispersion is centrifuged four times at 4° C., 4500 RZB and 210 r/mm. The supernatant containing the free carboxyfluorescein CF is removed after each centrifugation step and replaced by an equal volume of PBS buffer in which the liposomal pellet is resuspended.

To determine the encapsulation efficiency EE of different liposomal formulations of the present invention as depicted in FIG. 2 (cf. FIG. 1 and embodiments 1 to 3 for the composition of formulations), the concentration of non-encapsulated carboxyfluorescein $C_{free}$ as well as the total carboxyfluorescein concentration $C_{tot}$ is determined via fluorescence spectrometry. To measure the concentration of non-encapsulated carboxyfluorescein $C_{free}$, for example 100 µl of the liposomal dispersion are centrifuged and the concentration of carboxyfluorescein CF is determined in the supernatant. To determine the total carboxyfluorescein concentration $C_{tot}$, 900 µl of a 1% triton-X 100/PBS solution are added to 100 µl of the solution to be measured and shaken for 10 minutes at room temperature, which results in a release of the encapsulated carboxyfluorescein CF.

The drug encapsulation efficiency EE of liposomal formulations is then calculated according to the following equation and is indicated in percent [%]

$$EE[\%]=100*C_{encaps}/C_{start}$$

In this equation, $C_{encaps}$ denotes the concentration of encapsulated active compound and $C_{start}$ the concentration of active compound used for the preparation procedure (here 50 mg/ml). The concentration of encapsulated active compound $C_{encaps}$ is calculated according to the following equation:

$$C_{encaps}=C_{tot}-C_{free}$$

One can see that exemplarily shown liposomes of the present invention have an encapsulation efficiency EE of approximately 1 to 3% with regard to hydrophilic active compounds, which is typical for the film method.

The stability of liposomes during nebulization which is also depicted in FIG. 2 is calculated as follows. For a nebulization using a piezoelectric nebulizer (Aeroneb Pro®, Aerogen, Ireland), liposome suspensions as described above are diluted with PBS buffer to a final carboxyfluorescein CF concentration of 500 µg/ml, and 3 ml of the resulting solution are nebulized. Aerosol samples are taken by introducing a glass plate into the aerosol, followed by collecting the condensate which accumulates on the plate. For each of these samples, the content of free carboxyfluorescein $C_{free}$ as well as the total concentration of carboxyfluorescein $C_{tot}$ is determined as described above. The percentage of encapsulated carboxyfluorescein $CF_{lip}$ is then calculated according to the equation $$CF_{lip}=100\%*(C_{tot}-C_{free})/C_{tot}$$

The stability of liposomes during nebulization can be determined by comparing the amount of encapsulated carboxyfluorescein $CF_{lip}$pre determined prior to nebulization with the amount of encapsulated carboxyfluorescein $CF_{lip}$-post determined after nebulization.

The percentage of liposomes which remain stable during nebulization is given by the ratio 100*($CF_{lip}$post):($CF_{lip}$pre). It becomes evident that more than liposomes of the present invention exemplarily shown here have a stability of more than 80% during nebulization.

FIG. 2 furthermore demonstrates that also the size of liposomes according to the present invention is highly stable during nebulization. For this determination, 100 to 200 µl of the liposome dispersion are diluted before and after nebulization in 40 ml aqua dest. The median volume diameter MVD of liposomes is then measured using laser light scattering.

In addition, the size of aerosol particles as depicted in FIG. 3, which is an important factor for alveolar delivery of the inhalants, is determined by laser light scattering after nebulization of the liposomal formulation. It is evident that particles containing exemplarily shown liposomes of the present invention have a mass median aerodynamic diameter MMAD of approximately 4 µm and are thus well able to reach the alveolar spaces of the lung.

Column 1 of FIG. 3 indicates the mass median aerodynamic diameter and geometric standard deviation of particles of a nebulized 0.9% NaCl solution used as control, column 2 the mass median aerodynamic diameter and geometric standard deviation of particles of an aerosolized liposomal formulation known by the state of the art and comprising DPPC/DMPC and CHOL, column 3 the mass median aerodynamic diameter and geometric standard deviation of particles of a nebulized liposomal formulation comprising DSPC/DPPC and CHOL according to embodiment variant 1, column 4 the mass median aerodynamic diameter and geometric standard deviation of particles of a nebulized liposomal formulation comprising DSPC/DMPC and CHOL according to embodiment variant 2, and column 5 the mass median aerodynamic diameter and geometric standard deviation of particles of a nebulized liposomal formulation comprising DSPC/DPPE and CHOL according to embodiment variant 3.

For the determination of in vitro-drug release characteristics of liposomes of the present invention as depicted in FIGS. 4*a* and 4*b*, each 0.4 ml of a liposome suspension prepared as described above are diluted in a release medium to a volume of 10 ml. As release medium, either PBS with a pH value of 7.4 or a solution of 0.5 mg/ml Alveofact® in PBS is used. The dispersion prepared according to this protocol is incubated at 37° C. During the first hour, samples of 300 µl each are removed at 10 minutes intervals. During the second hour, 300 µl-samples are removed every 20 min and during the third hour, samples of 300 µl-samples are removed every 30 min. Immediately after removal, samples are each diluted with 4° C. PBS to a ratio of 1:20 and stored on ice in reaction tubes protected from light until the carboxyfluorescein release is measured fluorimetrically.

For the determination of drug release characteristics as depicted in FIG. 5, an isolated, perfused and ventilated rabbit lung is used as model (for a detailed description of this well known model system, see for example Lahnstein et al., International Journal of Pharmaceutics 351 (2008), pages 158 to 164). For inhalative administration, liposomal formulations are prepared as described above, diluted in PBS with a pH value of 7.4 and nebulized. The deposition of aerosol in the isolated organ is quantitatively determined and serves as basis for the calculation of the amount of drug compound or dye initially deposited in the lung. To determine how much of the active compound de facto remains in the lung after inhalative administration, samples are removed from the perfusate over a period of 300 minutes. The amount of active compound which was released during this time from the lung into the perfusate can thus be determined. Knowing the amount of active component initially deposited in the lung, the sustained release effect of the respective liposomal formulation can then be estimated. The amount of active compound remaining in the lung equates to the difference between initially deposited active compound and the amount of active compound released into the perfusate. The lower the amount of active compound released from the lung into the perfusate per time unit, the stronger is the sustained release effect of the inhaled liposomal formulation.

In FIGS. 4*a*, 4*b* and 5, graphs 6 show the cumulative release of CF from liposomes containing DPPC/DMPC/CHOL, graphs 7 cumulative release of CF from liposomes containing DSPC/DPPC/CHOL according to embodiment 1, graphs 8 cumulative release of CF from liposomes containing DSPC/DMPC/CHOL according to embodiment 2, graphs 9 cumulative release of CF from liposomes containing DSPC/DMPE/CHOL according to embodiment 3, and graphs 10 cumulative release of CF from a solution used as control, containing non-encapsulated CF.

FIGS. 4*a*, 4*b*, and 5 demonstrate that liposomes which—as initially described—are known by the state of the art and which are composed of a mixture of DPPC/DMPC and cholesterol, release the model compound carboxyfluorescein CF instantaneously and completely within a very short time in a form referred to as burst release. The release kinetic is in this case similar to the release kinetic of non-encapsulated free carboxyfluorescein CF. It becomes evident from the in vitro characteristics of FIGS. 4*a* and 4*b* that liposomes comprising DPPC/DMPC and cholesterol completely release the contained carboxyfluorescein CF immediately after incubation start. In contrast, a significantly slower release over a prolonged time can be observed in liposomes according to the present invention.

Liposomes known by the state of the art show also in the organ model a fast increase of carboxyfluorescein concentration in the perfusate. It becomes quite obvious that this increase is comparable to the increase of carboxyfluorescein concentration observed in the perfusate after inhalative administration of a solution of non-encapsulated carboxyfluorescein CF. Thus for both formulations, the CF concentration in the perfusate reaches a stable plateau of approximately 500 mg/ml after 140 minutes. Liposomes of the present invention (for example according to one of the embodiments 1, 2 or 3) however also show in the organ model a considerably slower increase of carboxyfluorescein concentration in the perfusate, and in each case the CF concentration is substantially lower at the end of the experiment after 300 minutes. From these data it becomes evident that if liposomal formulations according to the present invention are used, a considerably higher amount of carboxyfluorescein remains in the lung for a longer period of time in terms of a sustained release.

Summarizing, the advantage offered by liposomes of the present invention can clearly and well be deduced from FIGS. 4*a*, 4*b*, and 5, since said liposomes release only small amounts of active compound over a prolonged period of time, thus providing a sustained release. Looking at the following exemplary embodiment variants, further advantages become evident.

Embodiment Variant 1

As demonstrated in FIG. 1, liposomes according to the present invention can for example comprise distearoylphosphatidylcholine DSPC as first phospholipid, dipalmitoylphosphatidylcholine DPPC as second phospholipid and cholesterol CHOL in a molar ratio of DSPC:DPPC:CHOL=4:4:2. The first and the second phospholipid are thus present in a molar ratio of 1:1, the molar ratio of phospholipids to cholesterol amounts to 4:1.

The diameter of such liposomes after extrusion is 0.59±0.03 μm, after centrifugation 0.59±0.04 μm, and after nebulization 0.59±0.02 μm. It is thus evident that the size of liposomes according to the present invention is highly constant during nebulization.

The encapsulation efficiency is, as demonstrated in FIG. 2, in a range of 1.29±0.18%. The stability during nebulization also shown in FIG. 2 is determined by comparing the fraction of encapsulated model compound prior to nebulization $CF_{lip}$PRE, which is 96.1%, with the fraction of encapsulated model compound after nebulization $CF_{lip}$-POST, which is 79.1%. It can be seen that liposomes according to the present invention of this exemplary embodiment have a nebulization stability of more than 80%, namely 82%.

Aerosol particles which contain liposomes according to this embodiment show an MMAD of 4.08±0.04 μm at a GSD of 1.7 after nebulization with an Aeroneb® Professional Nebulizer System, as presented in FIG. 3. It is obvious that liposomes according to this invention can preferably be nebulized in a way that these liposomes are well able to reach the alveolar space of the lung, due to the size of the aerosol particles formed.

The calculated phase transition temperature of said liposomal formulation is approximately 53° C., the experimentally determined phase transition temperature is however 46° C. and thus above 37° C. This is particularly advantageous with respect to a sustained drug release, since liposomes remain adequately stable at body temperature and the drug compound enclosed is released slowly and in small amounts. This is demonstrated by the in vitro release characteristics as depicted in FIGS. 4*a* and 4*b* and also by the release characteristics determined in the organ model as depicted in FIG. 5.

Using a dispersion of liposomes of the present invention in PBS (cf. FIG. 4*a*), in vitro a continuously increasing amount of the model compound is released over the first two hours, until approximately 42% of the model compound is released at the end of the experiment after 300 minutes. If liposomes of the present invention are dispersed in a solution of PBS/surfactant, approximately 70% of the encapsulated model compound is released within the first to hours.

Assessing the drug release characteristics in the organ model (cf. FIG. 5), the formulation of this invention shows a considerably lower concentration of carboxyfluorescein in the perfusate as compared to state-of-the-art formulations. After approx. 160 min of perfusion, a plateau is reached with a carboxyfluorescein concentration of approx. 320 ng/ml in the perfusate. Until the end of the measurement, the concentration increases only slightly further to about 340 ng/ml. This shows that the release of CF into the lung of this liposomal formulation takes place in a delayed manner.

Embodiment Variant 2

According to a further embodiment example, liposomes of the present invention may also comprise distearoylphosphatidylcholine (DSPC) as first phospholipid, dimyristoylphosphatidylcholine (DMPC) as second phospholipid, and cholesterol in a molar ratio of DSPC:DMPC:CHOL=6:1:2. First and second phospholipid are thus present in a molar ratio of 6:1, while the molar ratio of phospholipids to cholesterol is 7:2 (=3.5:1).

The diameter of said liposomes after extrusion is in the range of 0.60±0.02 μm, after centrifugation 0.61±0.02 μm, and after nebulization 0.64±0.09 μm. It becomes evident that the size of liposomes according to the present invention remains highly constant during the nebulization process.

The encapsulation efficiency amounts to 1.99±0.21%, as demonstrated in FIG. 2. The stability during nebulization also shown in FIG. 2 is determined by comparing the fraction of encapsulated model compound prior to nebulization $CF_{lip}$PRE, which is 96.6%, with the fraction of encapsulated model compound after nebulization $CF_{lip}$-POST, which is 80.3%. It is obvious that liposomes of this exemplary embodiment according to the present invention show a stability of more than 80%, namely 83%, during nebulization.

Aerosol particles which contain liposomes according to this embodiment have an MMAD of 4.00±0.06 μm at a GSD of 1.7 after nebulization with an Aeroneb® Professional Nebulizer System, as depicted in FIG. 3. It is evident that liposomes of this invention can preferably be nebulized in a way that these liposomes are well able to reach the alveolar space of the lung, due to the size of the aerosol particles formed.

The calculated phase transition temperature of said liposomal formulation is 56° C. and thus above 37° C. This is particularly advantageous with respect to a sustained drug release, since liposomes remain adequately stable at body temperature and the drug compound enclosed is released only slowly and in small amounts. This is demonstrated by the in vitro release characteristics as shown in FIGS. 4*a* and 4*b* as well as by the release characteristics determined in the organ model as depicted in FIG. 5.

Using a dispersion of liposomes of the present invention in PBS (cf. FIG. 4*a*), in vitro a continuously increasing amount of the model compound is released over the first two hours, finally reaching a total of 18% model compound released at the end of the experiment after 300 minutes. If liposomes of the present invention are dispersed in a solution of PBS/surfactant, approximately 60% of the encapsulated model compound is released within the first to hours.

Assessing the drug release characteristics in the organ model (cf. FIG. 5), the formulation of this invention shows a considerably lower concentration of carboxyfluorescein in the perfusate as compared to state-of-the-art formulations. After approx. 160 min of perfusion, a plateau is reached at a carboxyfluorescein concentration of approx. 210 ng/ml in the perfusate. Until the end of the measurement, the concentration increases only slightly to about 240 ng/ml. This shows that the release of CF into the lung of this liposomal formulation takes place in a delayed manner.

Embodiment Variant 3

As depicted in FIG. 1, liposomes of the present invention comprise distearoylphosphatidylcholine DSPC as first phospholipid, dipalmitoylphosphatidylethanolamine DPPE as second phospholipid, and cholesterol in a molar ratio of DSPC:DPPE:CHOL=6:2:2. First and second phospholipid are thus present in a molar ratio of 3:1, the molar ratio of phospholipids to cholesterol is 4:1.

The diameter of liposomes after extrusion is in the range of 0.62±0.02 μm, after centrifugation 0.62±0.02 μm, and after nebulization 0.73±0.13 μm. It becomes evident that the size of liposomes according to the present invention remains highly constant during the nebulization process.

The encapsulation efficiency amounts to 2.78±0.30%, as demonstrated in FIG. 2. The stability during nebulization also shown in FIG. 2 is determined by comparing the fraction of encapsulated model compound prior to nebulization $CF_{lip}$PRE, which is 99.6%, with the fraction of encapsulated model compound after nebulization $CF_{lip}$-POST, which is 83.8%. It is obvious that liposomes of this exemplary embodiment according to the present invention show a stability of more than 80%, namely 84%, during nebulization.

Aerosol particles which contain liposomes according to this embodiment have an MMAD of 4.09±0.03 μm at a GSD of 1.8 after nebulization with an Aeroneb® Professional Nebulizer System, as depicted in FIG. 3. It can be seen that liposomes according to this invention can preferably be nebulized in a way that these liposomes are well able to reach the alveolar space of the lung, due to the size of the aerosol particles formed.

The calculated phase transition temperature of said liposomal formulation is 60° C., the experimentally determined phase transition temperature of liposomes is however approximately 55° C. and thus above 37° C. This is particularly advantageous with respect to a sustained drug release, since said liposomes remain adequately stable at body temperature and the drug compound enclosed is released slowly and in small amounts. This is demonstrated by the in vitro release characteristics as shown in FIGS. 4*a* and 4*b*, and also by the release characteristics determined in the organ model as depicted in FIG. 5.

Using a dispersion of said liposomes in PBS (cf. FIG. 4*a*), approximately 5% of the model compound was released after 300 minutes of observation time, while using a dispersion in PBS/surfactant, approximately 26% of the model compound was released over the same time period.

Assessing the drug release characteristics in the organ model (cf. FIG. 5), the formulation of this invention shows a considerably lower concentration of carboxyfluorescein in the perfusate as compared to state-of-the-art formulations. After approx. 110 min of perfusion, the carboxyfluorescein concentration in the perfusate increases to approx. 130 ng/ml, followed by a slower increase to a final concentration of 170 ng/ml after 300 minutes. This illustrates that the release of CF into the lung of this liposomal formulation takes place in a delayed manner.

The invention is not confined to one of the above-described embodiments, but may be modified in a wide variety of ways.

All features and advantages illustrated in the claims, the description and the figures, including design details, spatial arrangement and process steps, may be essential to the invention, either independently by themselves as well as combined with one another in any form.

Evident is that liposomes for pulmonary administration preferably comprise at least a first and at least a second phospholipid as well as cholesterol and at least one active compound and/or dye, whereby the first phospholipid is the phosphatidylcholine disteaorylphosphatidylcholine DSPC, and the second phospholipid is a phosphatidylcholine or an ethanolamine, preferably chosen from the group of dimyristoylphosphatidylcholine DMPC, dipalmitoylphosphatidylcholine DPPC, dipalmitoylphosphatidylethanolamine DPPE. It is further evident that the second phospholipid is preferably dimyristoylphosphatidylcholine DMPC or dipalmitoylphosphatidylethanolamine DPPE, particularly preferred dipalmitoylphosphatidylethanolamine DPPE. Advantageous is furthermore if the first and second phospholipid are present in a molar ratio of 0.5:1 to 10:1, preferred in a ratio of 6:1 to 2:1, particularly preferred in a molar ratio of 3:1. Favorable is furthermore if the molar ratio of phospholipids and cholesterol ranges between 10:1 and 1:1, preferred between 6:1 and 3:1, particularly preferred is a molar ratio of 4:1. Particularly preferred is also if said liposomes exhibit a stability of more than 50% during nebulization, preferred more than 75%, particularly preferred a stability of more than 80%. The size of liposomes thereby ranges between 0.05 μm and 5 μm, preferred between 0.2 μm and 2.0 μm, and the mass median aerodynamic diameter of aerosol particles which contain liposomes ranges from 1 μm to 6 μm, preferred from 1.5 μm to 5 μm, particularly preferred from 2 μm to 4.5 μm. It can be seen that it is of advantage if the size of liposomes after nebulization differs by less than 1 μm, preferably less than 0.2 μm from the size the size of liposomes before the nebulization process. Advantageous is also if the phase transition temperature is above 37° C., preferred above 45° C., particularly preferred above 50° C. Furthermore it is obvious that liposomes can be nebulized with piezoelectric, air-jet or ultrasonic nebulizers or with soft-mist inhalators.

Advantageously, the active compound is chosen from the group of appetite suppressants/antiadipose agents, acidose therapeutics, analeptics/antihypoxaemic agents, analgesics, antirheumatics, anthelmintics, antiallergics, antianemics, antiarrhythmics, antibiotics, antiinfectives, antidementives, antidiabetics, antidotes, antiemetics, antivertigo agents, antiepileptics, antihemorrhagic agents, haemostatics, antihypertensives, antihypoglycemics, antihypotensives, anticoagulants, antimycotics, antiparasitic agents, antiphogisitics, antitussives, expectorants, antiarteriosclerotics, beta-receptor blockers, calcium channel blockers, inhibitors of the renin-angiotensin-aldosterone system, broncholytics, antiasthma agents, cholagogics, bile duct therapeutics, cholinergics, corticoids, diagnostics and agents for diagnostic preliminaries, diuretics, circulation-promoting agents, antiaddiction agents, enzyme inhibitors, enzyme-activating or stimulating agents, enzyme deficiency correcting compounds, receptor antagonists, transport proteins, fibrinolytics, geriatric agents, gout agents, influenza drugs, colds and flu remedies, gynecologic agents, hepatics, hypnotics, sedatives, pituitary and hypothalamus hormones, regulatory peptides, hormones, peptide inhibitors, immunomodulators, cardiacs, coronary agents, laxants, lipid-reducing agents, local anaesthetics, neural therapeutic agents, gastric agents, migraine agents, mineral preparations, muscle relaxants, narcotics, neurotropic agents, osteoporosis remedies, calcium/calcium metabolism regulators, remedies for Parkinson's disease, psychopharmaceuticals, sinusitis agents, roborantia, thyroid therapeutics, serums, immunoglobulins, vaccines, antibodies, sexual hormones and their inhibitors, spasmolytics, anticholinergic agents, thrombocyte aggregation inhibitors, antituberculosis agents, urological agents, vein therapeutics, vitamins, cytostatics, antineoplastic agents, homeopathic remedies, vasoactive agents, gene therapeutics (DNA/RNA derivatives), transcription inhibitors, virostatics, nicotin, agents against erectile dysfunction, nitric oxide and/or nitric oxide-liberating substances. Advantageously, the active compound and/or dye can also comprise or contain magnetic particles.

Advantageous is furthermore a utilization of liposomes of the present invention for the preparation of a pharmaceutical composition for the prevention, diagnosis and/or treatment of lung diseases and/or systemic diseases. Of particular advantage is the utilization of said liposomes for the preparation of a pharmaceutical composition for the prevention, diagnosis and/or treatment of diseases of the alveolar space, the utilization of said liposomes for the preparation of a pharmaceutical composition for the prevention, diagnosis and/or treatment of respiratory tract diseases and the utilization of said liposomes for the preparation of a pharmaceutical composition for the prevention, diagnosis and/or treatment of pulmonary hypertension.

ABBREVIATIONS AND REFERENCE SIGN LIST

| | | | |
|---|---|---|---|
| DSPC | Disteaorylphosphatidylcholine | $CF_{encaps}$ | Amount of encapsulated active compound |
| DPPC | Dipalmitoylphosphatidylcholine | | |
| DMPC | Dimyristoylphosphatidylcholine | $CF_{tot}$ | Total concentration of active compound |
| DPPE | Dipalmitoylphosphatidyl-ethanolamine | $CF_{free}$ | Concentration of free active compound |
| P1 | First phospholipid | | |
| P2 | Second phospholipid | $CF_{lip}$PRE | Fraction of encapsulated active compound prior to nebulization |
| PL | Phospholipids | | |
| Chol | Cholesterol | $CF_{lip}$POST | Fraction of encapsulated active compound after nebulization |
| EE | Encapsulation efficiency | | |
| CF | Carboxyfluorescein | MMAD | Mass median aerodynamic diameter |
| $CF_{start}$ | Amount of active compound before removal of non-encapsulated drug | | |
| | | MVD | Median volume diameter |
| | | GSD | Geometric standard deviation |
| | | Neb. | Nebulization |

1. Mass median aerodynamic diameter and geometric standard deviation of particles of an aerosolized solution of 0.9% NaCl 2. Mass median aerodynamic diameter and geometric standard deviation of particles of an aerosolized liposomal formulation comprising DPPC/DMPC and CHOL 3. Mass median aerodynamic diameter and geometric standard deviation of particles of an aerosolized liposomal formulation comprising DSPC/DPPC and CHOL 4. Mass median aerodynamic diameter and geometric standard deviation of particles of an aerosolized liposomal formulation comprising DSPC/DMPC and CHOL 5. Mass median aerodynamic diameter and geometric standard deviation of particles of an aerosolized liposomal formulation comprising DSPC/DPPE and CHOL 6. Cumulative release of CF from liposomes comprising DPPC/DMPC/CHOL 7. Cumulative release of CF from liposomes comprising DSPC/DPPC/CHOL 8. Cumulative release of CF from liposomes comprising DSPC/DMPC/CHOL 9. Cumulative release of CF from liposomes comprising DSPC/DMPE/CHOL 10. Cumulative release of CF from a solution comprising non-encapsulated CF

The invention claimed is:

1. A method of pulmonary administration comprising administering to a subject in need thereof via inhalation a liposomal formulation comprising:

A) liposomes comprising:
  i) a first phospholipid, which is disteaorylphosphatidylcholine;
  ii) a second phospholipid selected from the group consisting of dimyristoylphosphatidylcholine, dipalmitoylphosphatidylcholine, and dipalmitoylphosphatidylethanolamine; and
  iii) cholesterol; and B) an aqueous solution comprising at least one of an active agent and a dye, said aqueous solution being encapsulated inside said liposomes, wherein a molar ratio between the first phospholipid and the second phospholipid in the liposomes is from 2:1 to 6:1, wherein a molar ratio between a) the first and the second phospholipids and b) the cholesterol in the liposomes is from 3:1 to 6:1, wherein said administering comprises inhalation of said liposomal formulation after nebulization, and wherein a stability of said liposomes upon nebulization is at least 80%.

2. The method of claim 1, wherein the liposomes consist of the first phospholipid, the second phospholipid, and the cholesterol.

3. The method of claim 1, wherein the second phospholipid is selected from the group consisting of dimyristoylphosphatidylcholine and dipalmitoylphosphatidylcholine.

4. The method of claim 1, wherein a mass median aerodynamic diameter of aerosol particles produced by said nebulizing is between 1 μm and 6 μm.

5. The method of claim 4, wherein the mass median aerodynamic diameter of aerosol particles produced by said nebulizing is between 1.5 μm and 5 μm.

6. The method of claim 5, wherein the mass median aerodynamic diameter of aerosol particles produced by said nebulizing is between 2 μm and 4.5 μm.

7. The method of claim 1, wherein a size of the liposomes after the nebulizing differs from a size of the liposomes before the nebulizing by less than 1 μm.

8. The method of claim 7, wherein the size of the liposomes after the nebulizing differs from the size of the liposomes before the nebulizing by less than 0.2 μm.

9. The method of claim 1, wherein said nebulizing is performed by a piezoelectric nebulizer.

10. The method of claim 1, wherein said nebulizing is performed by an air-jet nebulizer.

11. The method of claim 1, wherein said nebulizing is performed by an ultrasonic nebulizer.

12. The method of claim 1, wherein a size of said liposomes ranges between 0.05 μm and 5 μm.

13. The method of claim 12, wherein a size of said liposomes ranges between 0.2 μm and 2.0 μm.

14. The method of claim 1, wherein a phase transition temperature of the liposomes is higher than 37° C.

15. The method of claim 14, wherein the phase transition temperature of the liposomes is higher than 45° C.

16. The method of claim 15, wherein the phase transition temperature of the liposomes is higher than 50° C.

17. The method of claim 1, wherein the active agent is an image-producing agent.

18. The method of claim 1, wherein the active agent is a radioactive agent.

19. The method of claim 1, wherein the active agent is a contrast agent.

20. The method of claim 1, wherein the active agent comprises magnetic particles.

21. The method of claim 1, wherein the active agent comprises treprostinil.

22. The method of claim 1, wherein the active agent comprises iloprost.

23. The method of claim 1, wherein the active agent comprises sildenafil.

24. The method of claim 1, wherein the liposomal formulation is a liposomal dispersion, which comprises an aqueous medium, in which the liposomes are dispersed.

* * * * *